United States Patent
Khan et al.

(10) Patent No.: US 6,936,065 B2
(45) Date of Patent: Aug. 30, 2005

(54) STENT DELIVERY SYSTEM HAVING A FIXED GUIDEWIRE

(75) Inventors: I. John Khan, Bridgewater, NJ (US); Robert Burgermeister, Bridgewater, NJ (US); Robert E. Fischell, Dayton, MD (US); David R. Fischell, Fair Haven, NJ (US)

(73) Assignee: Cordis Corporation, Miami Lakes, FL (US)

( * ) Notice: Subject to any disclaimer, the term of this patent is extended or adjusted under 35 U.S.C. 154(b) by 143 days.

(21) Appl. No.: 10/158,714

(22) Filed: May 30, 2002

(65) Prior Publication Data

US 2002/0147491 A1 Oct. 10, 2002

Related U.S. Application Data (63) Continuation-in-part of application No. 09/444,104, filed on Nov. 22, 1999, now Pat. No. 6,375,660, and a continuation-in-part of application No. 10/107,221, filed on Mar. 26, 2002.

(51) Int. Cl.[7] .................................................. A61F 2/06
(52) U.S. Cl. ...................... 623/1.11; 623/1.24; 606/108
(58) Field of Search ............................... 623/1.11, 1.24; 606/108, 194, 191, 192, 193, 195, 198, 113; 604/103.04, 103.05, 103.08

(56) References Cited

U.S. PATENT DOCUMENTS

| | | | | |
|---|---|---|---|---|
| 5,275,622 A | * | 1/1994 | Lazarus et al. | 623/1.11 |
| 5,562,728 A | * | 10/1996 | Lazarus et al. | 623/1.14 |
| 5,681,344 A | | 10/1997 | Kelly | |
| 6,066,133 A | * | 5/2000 | Guglielmi et al. | 606/32 |
| 6,123,723 A | * | 9/2000 | Konya et al. | 623/1.11 |
| 6,254,627 B1 | * | 7/2001 | Freidberg | 623/1.11 |
| 6,280,412 B1 | * | 8/2001 | Pederson, Jr. et al. | 604/103.07 |
| 6,368,344 B1 | * | 4/2002 | Fitz | 623/1.11 |
| 2002/0147491 A1 | | 10/2002 | Fischell et al. | |

FOREIGN PATENT DOCUMENTS

| | | |
|---|---|---|
| EP | 0 508 473 A | 10/1992 |
| EP | 1 101 455 A | 5/2001 |
| WO | WO 96/39999 A | 12/1996 |

OTHER PUBLICATIONS

European Search Report, dated May 26, 2003, for European Appln. No. EP 0 25 1908.
European Search Report, dated Oct. 27, 2003, for European Appln. No. EP 03 26 3353.

* cited by examiner

*Primary Examiner*—Pedro Philogene (57) ABSTRACT

The present invention is a stent delivery system that uses short section of guidewire fixedly attached to the distal section of a balloon angioplasty catheter onto which a stent is co-axially mounted. By not having a guidewire that slides through the balloon of the balloon angioplasty catheter, the deflated balloon on which the stent is mounted can have a reduced diameter. Therefore, the outer diameter of the pre-deployed stent mounted onto that balloon is also minimized. This provides a smaller profile, i.e., a smaller outer diameter, for the stent. The time to perform a stent delivery procedure is reduced; a separate guidewire does not have to be placed prior to using the stent delivery system to place the stent at the site of a stenosis. Another embodiment of the present invention has a core wire that extends for nearly the entire length of the stent delivery system, the guidewire having different levels of stiffness for different portions of the core wire's length.

18 Claims, 5 Drawing Sheets

STENT DELIVERY SYSTEM HAVING A FIXED GUIDEWIRE

REFERENCE TO PRIOR APPLICATION

This application is a continuation-in-part of U.S. patent application Ser. No. 09/444,104 filed on Nov. 22, 1999 now U.S. Pat. No. 6,375,660, and Ser. No. 10/107,221, filed Mar. 26, 2002, pending.

FIELD OF USE

This invention is in the field of devices for percutaneous insertion into a vessel of the human body to place a stent at the site of an obstruction.

BACKGROUND OF THE INVENTION

Stents are well known devices for placement in vessels of the human body to obtain and maintain patency of that vessel. The greatest use for stents has been for placement within a stenosis in a coronary artery. When a stent is used for treating a coronary artery stenosis, it has always been necessary to first place a guidewire through the stenosis. The next step in the stenting procedure may be to pre-dilate the stenosis with a balloon angioplasty catheter that is advanced over that guidewire. The catheter may be of the over-the-wire or rapid exchange variety. The balloon angioplasty catheter is then removed and a stent delivery system which includes the stent is advanced over the guidewire, and the stent is then deployed at the site of the dilated stenosis.

Recent improvements in the design of stent delivery systems have made it possible to eliminate the step of pre-dilatation for the treatment of many classes of stenoses. The delivery of a stent to the site of a stenosis without pre-dilatation has been commonly referred to as "direct stenting". However, even with direct stenting, a guidewire is still required as a precursor to advancing the stent delivery system over that guidewire to place the stent at the site of a stenosis. Placing the guidewire requires additional procedure time.

SUMMARY OF THE INVENTION

The present invention is a stent delivery system that uses short section of guidewire fixedly attached to the distal section of a balloon angioplasty catheter onto which a stent is co-axially mounted. By not having a guidewire that slides through the balloon of the balloon angioplasty catheter, the deflated balloon on which the stent is mounted can have a reduced diameter. Therefore, the outer diameter of the pre-deployed stent mounted onto that balloon is also minimized. This provides a smaller profile, i.e., a smaller outer diameter, for the stent. A minimum profile at the distal section of the stent delivery system is highly advantageous for improving the percentage of cases that can be treated by means of direct stenting; i.e., without requiring pre-dilation of a stenosis. An advantage of the present invention is that a separate guidewire is eliminated, thus saving any costs associated with such a guidewire. Additionally, the time to perform a stent delivery procedure is reduced; a separate guidewire does not have to be placed prior to using the stent delivery system to place the stent at the site of a stenosis.

One embodiment of the present invention uses a core wire that extends for the entire length of the stent delivery system. This core wire is also centrally located in the fixed guidewire that extends from the distal end of the balloon onto which the stent is mounted. Although this core wire can be made from a conventional metal such as stainless steel, the use of shape memory metal alloys (such as the nickel titanium alloy known as Nitinol) is ideal for such a core wire.

Furthermore, in a preferred embodiment of this invention, the Nitinol used for the fixed guidewire portion of the stent delivery system should have a transition temperature that is greater than body temperature. Therefore, prior to insertion, the interventional cardiologist who inserts the stent delivery system can make an appropriate bend into the end of the guidewire in order to maneuver the end of the guidewire into a specific artery. If the guidewire becomes damaged in passing through some difficult vasculature, the present invention describes the use of a special heater that can then be used to heat the guidewire to a temperature above its transition temperature, so that the guidewire would have its pre-damaged shape restored. Typically, the pre-damaged state would be a substantially straight wire or a wire with a slight, pre-set bend. After the guidewire cools below body temperature, the guidewire could then be reshaped again by the interventional cardiologist, to once again try to navigate through some tortuous part of the vasculature.

In a Nitinol implementation of the core wire of the stent delivery system, most of the core wire that lies proximal to the proximal end of the guidewire should have a transition temperature below body temperature. Therefore, the super-elastic properties of the Nitinol core wire proximal section will greatly reduce the probability of any kinking of the core wire that might occur if the metal were stainless steel.

Another embodiment of the present invention has a core wire that extends for nearly the entire length of the stent delivery system, the guidewire having different levels of stiffness for different portions of the core wire's length. For example, the proximal section should be extremely "pushable" would be the most stiff. The portion that lies within the balloon expandable stent should be very flexible, since the stent would be able to provide the needed "pushability". The present invention envisions that the variations in stiffness may be accomplished by changing the diameter of the core wire or by using different materials for different sections of the core wire.

Thus an object of the present invention is to provide a means for placing a stent within a vessel of the human body without requiring a separate guidewire, thus saving the cost of the guidewire and also saving the time required to place a separate guidewire through an obstruction such as an arterial stenosis.

Another object of the present invention is to reduce the outside diameter (i.e., the profile) of the distal section of the stent delivery system so as to optimize the capability of the stent delivery system for direct stenting.

Still another object of the present invention is to have a guidewire fixed at the end of a balloon angioplasty catheter with a stent co-axially mounted onto the catheter's inflatable balloon, and further that the length of the cylindrical portion of the inflated balloon that extends beyond each end of the stent (the "balloon overhang") is less than 1.0 mm, preferably less than 0.5 mm and optimally nearly 0 mm; the minimum balloon overhang being advantageous for reducing any likelihood of arterial wall dissection beyond the edges of the stent when the balloon is inflated.

Still another object of this invention is to have a core wire extending through most of the length of the fixed wire stent delivery system, the core wire being made from a shape memory alloy such as Nitinol with a transition temperature for the fixed guidewire region of the core wire being higher than body temperature, and most of the proximal portion of the core wire having a transition temperature below body temperature.

Still another object of this invention is to have a core wire extending through most of the length of fixed wire stent delivery system, the core wire having different portions each with different cross sectional areas thereby providing different levels of stiffness.

Yet another object of this invention is to have the proximal section of the core wire be the stiffest part of the core wire, in order to enhance system pushability.

Yet another object of this invention is to have the section of the core wire that lies within the balloon expandable stent be significantly less stiff than portions of the core wire that lie proximal to the balloon. These and other important objects and advantages of this invention will become apparent from the detailed description of the invention and the associated drawings provided herein.

DETAILED DESCRIPTION OF THE INVENTION

Figure 1:
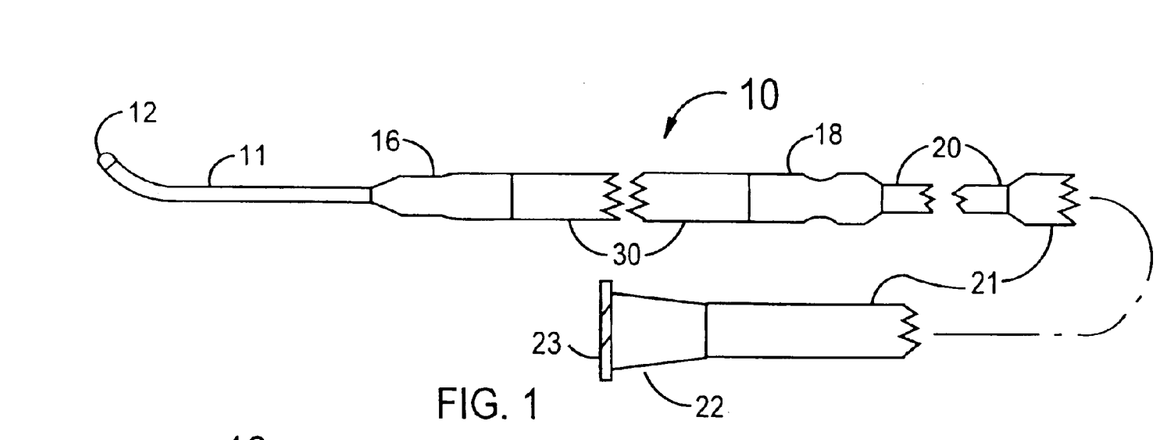
FIG. 1 is a side view of a stent delivery system having a balloon angioplasty catheter and having a fixed guidewire extending beyond the distal end of the balloon angioplasty catheter.
Figure 2:
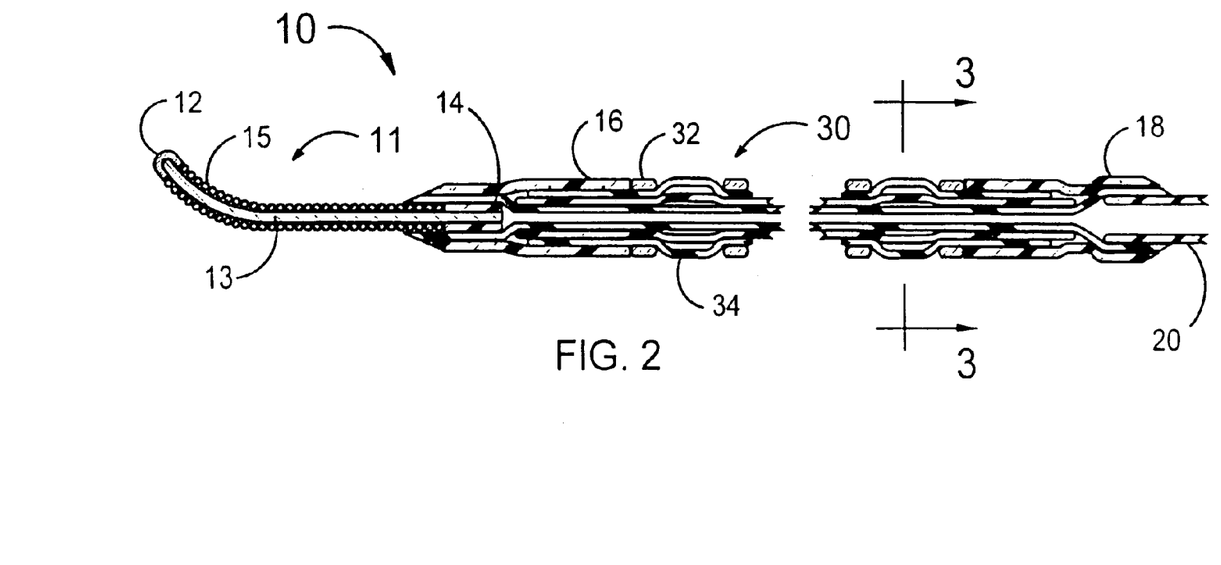
FIG. 2 is a longitudinal cross section of the distal section of the stent delivery system that is shown in FIG. 1.

FIGS. 1 and 2 illustrate a stent delivery system 10 having a fixed guidewire 11 that is fixedly attached to the distal end of a balloon angioplasty catheter that has a minimum profile for the distal section of the balloon angioplasty catheter. The distal section of the stent delivery system 10 includes a guidewire 11, a proximal elastic band 18, a stent-on-balloon section 30 and a distal elastic band 16. The stent-on-balloon section 30 includes an inflatable balloon 34 onto which a balloon expandable stent 32 is co-axially mounted. A cylindrically shaped distal section of the balloon 34 is fixedly attached to a proximal section of the guidewire 11 that includes a plastic cylinder 14 that is fixedly attached to a central core wire 13 of the guidewire 11.

A helical wire coil 15 is wrapped around the core wire 13 for most of the length of the core wire 13. The outside diameter of the guidewire 11 would typically be 0.014 inches. However, outside diameters between 0.008 and 0.035 inches could be used. The diameter of the core wire 13 would typically be between 0.002 and 0.014 inches. However, it should be understood that the core wire 13 could have a tapered section and could also have a flattened or square cross section situated within the wire coil 15. The flattened section of the core wire 13 is ideally suited for retaining a bend that is created by the doctor just before placing the stent delivery system 10 into a vessel of a human subject.

The material of the guidewire 11 would typically be stainless steel, tantalum, Nitinol or a combination of such metals. A distal section of the guidewire 11 could be substantially straight or it could be substantially curved as generally indicated in FIGS. 1 and 2. The curve could be as supplied by the manufacturer or it could be made or adjusted by the person (typically an interventional cardiologist) placing the stent delivery system 10 into the patient. The length of the guidewire 11 that lies distal to the distal end of the balloon 34 should be approximately 1.0 to 2.0 cm and certainly less than 5 cm. Furthermore, a plastic layer with a lubricious outer surface could be substituted for the helical wire coil 15. It is also envisioned that the coil 15 could be coated with Teflon® or another lubricious material.

A proximal section of the balloon 34 is fixedly attached to a distal section of a central cylindrical tube 20. The central cylindrical tube 20 would typically be formed from a plastic material such as polyurethane, polyethylene, nylon, Teflon®, or any of the many similar polymeric materials used for balloon angioplasty catheters. The outside diameter of the tube 20 would typically be between 0.5 and 2.0 mm. The length of the tube 20 would typically be between 10 and 40 cm.

The central tube 20 can be joined at its proximal end to the distal end of a proximal cylindrical tube 21. It is envisioned that the proximal tube 21 would extend for most of the length of the stent delivery system 10. A Luer fitting 22 located at the proximal end of the proximal tube 21 would be used for fluid connection by means of the attachment thread 23 to a stop-cock (not shown) to which a syringe can be attached that provides a source of inflation fluid for the balloon 34. The syringe or a fluid pumping device that includes a pressure gauge can be used to inflate the balloon 34 with contrast medium to deploy the stent 32 into a stenosis. The syringe or pumping device would also be used to deflate the balloon 34 after the stent 32 has been deployed.

Figure 3:
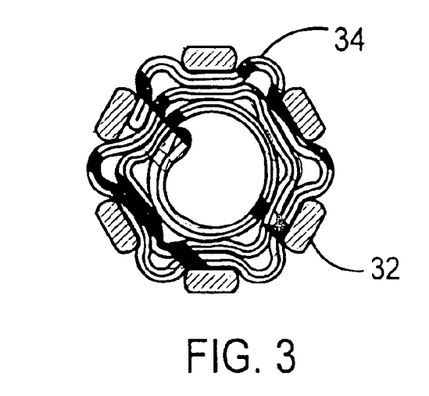
FIG. 3 is an enlarged transverse cross section of the distal section of the stent delivery system at section 3—3 of FIG. 2.

FIG. 2 shows three layers of the balloon 34, which layers would typically be formed by rolling the balloon 34 in a spiral manner (like a "jellyroll") as seen in FIG. 3. For the sake of clarity, only three layers are shown in FIG. 2 on each side of the balloon 34. [To be technically correct, six layers should be shown in FIG. 2 on each side of the balloon 34.] Although FIG. 3 shows a rolled balloon 34, it should be understood that a conventional balloon made with a multiplicity of folded wings could also be used.

It should be understood that a conventional guidewire must be able to be rotated in order to place it into a specific artery that has the stenosis that is to be treated. To be effective as a stent delivery system for direct stenting, the stent delivery system 10 must have the capability to apply torque to the guidewire 11 so that the guidewire's distal tip 12 can be selectively advanced at an arterial bifurcation into the branch artery that is to be stented.

When the stent delivery system is percutaneously placed into a vessel of a human body, the Luer fitting 22 remains exterior to that body, where it can be held and rotated by the physician in order to apply a torque to rotate the distal end 12 of the guidewire 11. When a twist is applied to the Luer fitting 22, the spiral-shaped balloon 34 would tend to form a tightened spiral or would loosen depending upon the direction of the twist that is applied. By having the proximal elastic band 18 and distal elastic band 16 shrunk onto the portions of the balloon 34 that have the shape of a frustum of a cone when the balloon 34 is inflated, loosening of the spiral shape of the folded balloon 34 is prevented even if the direction of twist applied to the Luer fitting 22 would otherwise have unwound that spiral. In this manner, the structure shown in FIGS. 1 and 2 is capable of using the Luer fitting 22 to apply the twist that is required for positioning the guidewire 11 into virtually any arterial stenosis selected for direct stenting.

It should be noted that the elastic bands 16 and 18 should be made from an elastomer such as silicone rubber. The portion of the band that lies over the balloon 34 can expand radially when the balloon 34 is inflated to deploy the stent 32. The elastic bands 16 and 18 could be solvent swelled and then placed in position or heat shrinking could be used for their placement. In either case, after placement they would snugly fit onto the balloon 34 as shown in FIGS. 1 and 2. Furthermore, the band 16 could be adhesively bonded to the guidewire 11 and/or the balloon 34. The band 18 can be adhesively bonded to the central tube 20.

Figure 4:
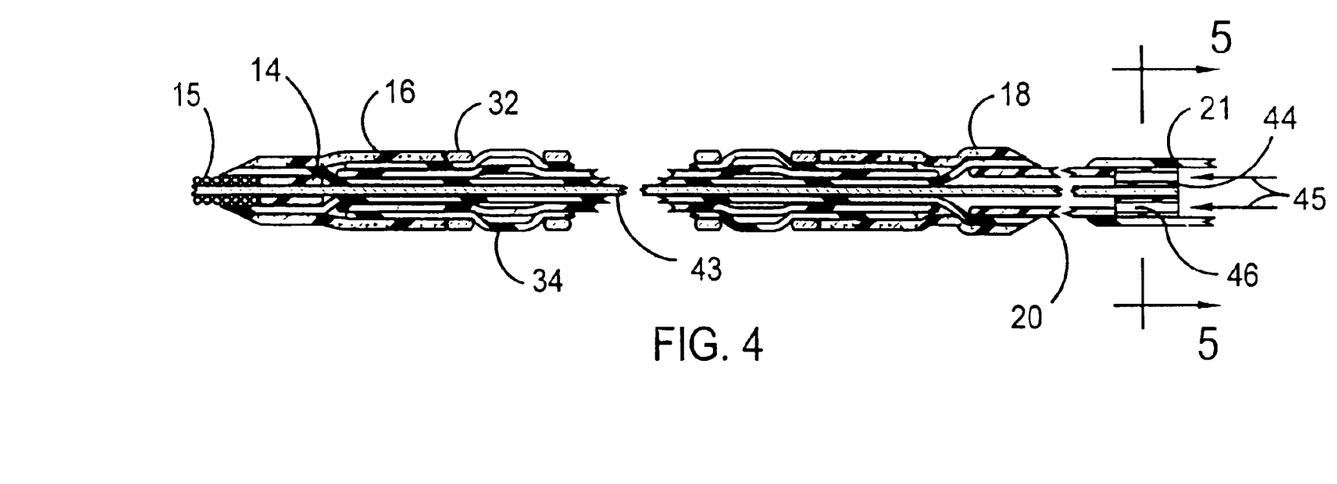
FIG. 4 is a longitudinal cross section of another embodiment of the present invention that utilizes an elongated core wire.
Figure 5:
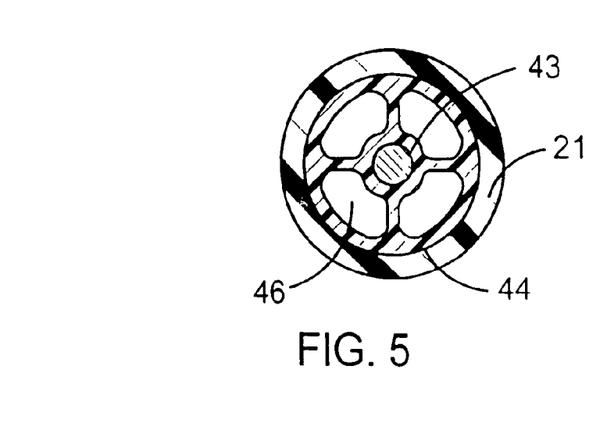
FIG. 5 is an enlarged transverse cross section of the stent delivery system at section 5—5 of FIG. 4 showing the connection between elongated core wire and the proximal tube of the stent delivery system.

Another embodiment of the present invention is shown in FIGS. 4 and 5. This embodiment differs from the embodiment of FIGS. 1 and 2 in that the core wire 13 of FIG. 1 and 2 is considerably lengthened. The elongated core wire 43 of FIGS. 4 and 5 extends through the balloon 34, into, and through the central tube 20. Although the elongated core wire 43 could have its proximal end terminate within the central tube 20, it would more advantageously extend into the proximal tube 21. The core wire 43 could even extend to the Luer fitting 22. The proximal end of the core wire 43 can be fixedly attached to a cylindrical, multi-lumen connector 44 that has lumens 46 through which fluid can be passed to inflate and deflate the balloon 34. The arrows 45 indicate the direction of fluid flow for inflating the balloon 34. The purpose of the elongated core wire 43 is to provide additional pushability and also to enhance the transmission of torque to the guidewire 11. Another purpose of the core wire 43 is to prevent inadvertent separation of the guidewire 11 from the stent delivery system 10.

An important feature of the stent delivery system 10 would be to minimize the length of the cylindrical portion of the balloon 34 that extends beyond each end of the stent 32 when the balloon is inflated. This length is called "balloon overhang". Because the guidewire 11 cannot remain in the treated stenosis after the stent delivery system 10 is taken out of the patient, it is important that edge dissections of the arterial wall that occur more frequently with longer lengths of balloon overhang be avoided. To accomplish a reduced occurrence of stent edge dissections, balloon overhang of the balloon 34 at each end of the stent 32 should be less than 1.0 mm and preferably less than 0.5 mm. Ideally, the balloon overhang should be 0±0.5 mm. How to achieve reduced balloon overhang is explained in detail in the U.S. patent application Ser. No. 09/373,552, entitled "Stent Delivery Catheter with Enhanced Balloon Shape", incorporated herein by reference.

In FIGS. 2, 3 and 4, the balloon 34 is shown to bulge outwardly between the struts of the stent 32. This method for holding the stent 32 more securely onto the balloon 34, is called "nesting". It is understood that the stent 32 could either be mechanically crimped onto the balloon 34 or it could be nested.

It should be understood that the proximal tube 21 could extend from the proximal end of the balloon 34 to the Luer fitting 22 that is situated at the proximal end of the stent delivery system 10. That is, this invention will function satisfactorily without having a central tube 20. Furthermore, wire reinforcing in the wall of either or both the tube 20 or the tube 21 is envisioned for improving the pushability of the stent delivery system 10.

Figures 6, 7, 8:
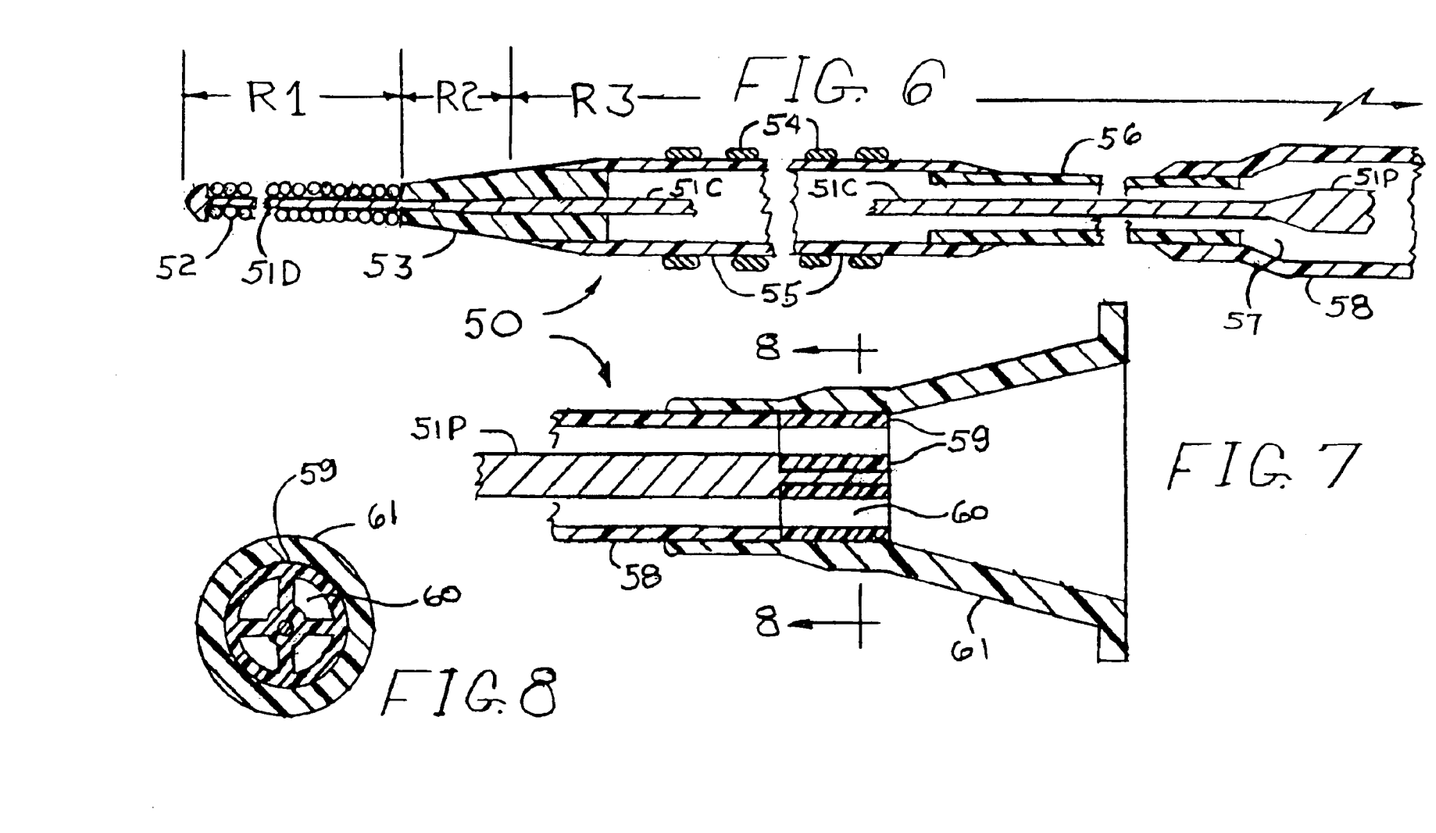
FIG. 6 is a longitudinal cross section of the distal portion of another embodiment of the present invention that has an elongated core wire extending to the proximal end of the stent delivery system.
FIG. 7 is a longitudinal cross section of the proximal portion of the embodiment of the present invention of FIG. 6 showing the elongated core wire extending to near the proximal end of the stent delivery system.
FIG. 8 is a transverse cross section of the stent delivery system at section 8—8 of FIG. 7.

FIGS. 6, 7 and 8 illustrate an additional embodiment of the present invention. Specifically, FIGS. 6 and 7 are longitudinal cross-sections of a stent delivery system 50 that has an improved metal core wire. Although they are not shown in FIG. 6, it is clearly envisioned that elastic bands such as the elastic bands 16 and 18 of FIGS. 1 and 2 could also be used with the stent delivery system 50 of FIG. 6. The stent delivery system 50 has a fixed guidewire 52 with a centrally located distal core wire portion 51D to which a conically shaped plastic piece 53 is attached. The inflatable balloon 55 is joined at its distal end to the plastic piece 53 and joined at its proximal end to a central tube 56. A pre-deployed stent 54 is co-axially mounted onto the balloon 55. Preferably, the stent 54 would be coated with a drug eluting coating such as the drug sirolimus.

The central tube 56 connects at its proximal end to the distal end of the proximal tube 58. The proximal end of the proximal tube 58 is fixedly joined to a Luer fitting 61 and also connected to a multi-lumen connector 59 having pass-through lumens 60. The transverse cross section of the multi-lumen connector 59 is shown in FIG. 8. The proximal end of the proximal core wire portion 51P can have a reduced diameter at its proximal end where it is fixedly attached to the multi-lumen connector 59. Fluid can be injected through the Luer fitting 61 to inflate the balloon 55 and deploy the stent 54. This fluid would pass through the lumens 60 and the passageway 57 and into the balloon 55. The balloon 55 would be deflated by pulling the fluid out through the Luer fitting 61.

The core wire of the stent delivery system 50 is formed in three parts, namely a distal core wire portion 51D, a central core wire portion 51C and a proximal core wire portion 51P. The distal core wire portion 51D is centrally located with the fixed guidewire 52 located at the distal end of the stent delivery system 50. As with the embodiment of FIGS. 1–4, the cross section of the of the core wire portion 51D of the fixed guidewire could be flat, square or round. The fixed guidewire 52 has a distal region R1 and a proximal region R2. The central core wire portion 51C extends in the region R3 with an essentially uniform diameter from the proximal end of distal region R2 to where the core wire diameter increases to become the proximal core wire portion 51P.

Although the core wire could be formed from a conventional metal such as stainless steel, optimally the core wire would be fabricated from a shape memory alloy such as Nitinol. An optimum design for a Nitinol core wire would have the distal region R1 having a transition temperature that is higher than the temperature of the human body. For example, the transition temperature for the region R1 would be greater than 105° F. and optimally approximately 115° F.

Thus, if the guidewire 52 is bent by the interventional cardiologist as might be needed for entering a particular branch of the coronary arteries, that bend would be maintained even at body temperature.

The region R3 would have a transition temperature that is below body temperature so that any kinking of the core wire that is proximal to the proximal end of the region R2 would be automatically straightened when the stent delivery system 50 is placed into a human subject. A typical transition temperature for the region R3 could be approximately 80° F. to 90° F. from its martensitic crystalline state to its austenitic crystalline state.

The region R2 would be designed such that the transition temperature at its distal end would be the same as the transition temperature of the region R1, and the transition temperature at its proximal end would be the same as for the region R3. Thus, there would be a change in the transition temperature from somewhat above body temperature at the distal end of the region R2 to a transition temperature somewhat below body temperature at the proximal end of the region R2. Thus, any kinking of the core wire proximal to region R2 would automatically be straightened when the stent delivery system 50 was placed into the human subject. Furthermore, the interventional cardiologist could put whatever bend he wished into the region R1 without that bend changing shape when the stent delivery system 50 is placed into the human subject.

The fixed guidewire 52 has, for most of its length, a helical metal coil that surrounds the core wire 51D. Although this coil is typically formed from stainless steel, it could also be formed from Nitinol or more optimally from a highly radiopaque metal such as the alloy L605 or MP35N, or the element tantalum. In any case, the outer surface of the coil should be coated with a lubricious plastic such as Teflon®.

Because the outer surfaces of the central tube 56 and the proximal tube 58 each will make contact with the inner surface of a guiding catheter or the inner surface of curved coronary arteries, there can be a considerable degree of fiction between those tubes 56 and 58 and their surroundings. To provide the best control of the angular position of the fixed guidewire 52, it is desirable to exert the torque to control the angular position of the guidewire 52 by means of the core wire that extends from the proximal end of the guidewire 52 to the proximal end of the stent delivery system 50. By coating the entire outer surface of the core wire including the sections 51C and 51P and/or coating the inner surfaces of the central tube 56 and proximal tube 58 with a lubricious coating, any frictional resistance between the core wire and the tubes 56 and 58 would be greatly reduced. By applying such lubricious coating(s), the core wire could more readily transfer a torque from the core wire's proximal end to the fixed guidewire 52 and therefore, the angular placement of the guidewire 52 could be more readily controlled.

It would be highly undesirable to have to discard the stent delivery system 50 with its stent 54, if the guidewire 52 became bent or kinked when pushed through a tortuous coronary artery prior to delivering the stent 54 into an arterial stenosis.

Figure 9:
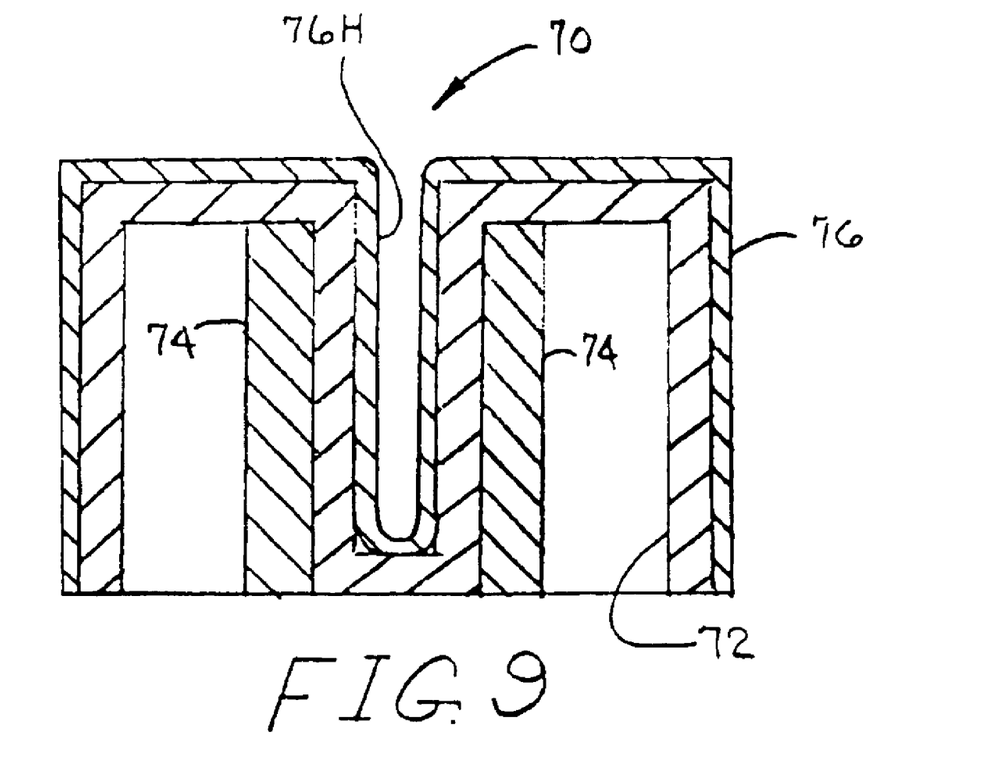
FIG. 9 is a cross section of a heating unit for raising the temperature of the distal portion of the core wire of the stent delivery system (i.e., the fixed guidewire).

In the case where the guidewire 52 is made of Nitinol, if such damage to the guidewire 52 were to occur, the heater 70 of FIG. 9 could be used to restore the shape of the guidewire 52. By exposing the guidewire 52 to a temperature that exceeds the transition temperature of the Nitinol in the region R1 the guidewire 52 would return to a straightened, pre-formed state.

The heater 70 would be used only if there was some significant kinking of the guidewire 52. The heater 70 has a generally cylindrical body 72, generally cylindrical, thermostatically controlled heating elements 74 and a sterile cover 76 having a hole 76H into which the guidewire 52 could be placed if it became damaged. For more rapid heat transfer into the guidewire 52, the hole 76H could be filled with a sterile saline solution that is readily available in a catheterization laboratory. Exposing the guidewire 52 to a temperature above the transition temperature of the distal core wire portion 51D in the region R1 would restore the guidewire 52 to its original shape prior to the interventional cardiologist having placed the stent delivery system 50 into the human subject. After the guidewire 52 is removed from the heater 70 and returns to a temperature below body temperature, the interventional cardiologist would be able once again to reshape the guidewire 52 to allow the distal end of the stent delivery system 50 to be maneuvered to a specific location in the coronary vasculature.

One of the goals of the present invention is to have a minimum outside diameter for the stent mounted onto the balloon to allow for easy delivery into even small or highly curved coronary arteries. Therefore, it is important that the wall thickness of the stent be as small as possible within the constraint of achieving adequate radial rigidity for dilating an arterial stenosis. Although stainless steel could be used for this purpose, improved radiopacity for such a thin-walled stent could be better achieved by using a metal having a higher density, such as the materials previously noted.

Figure 10:
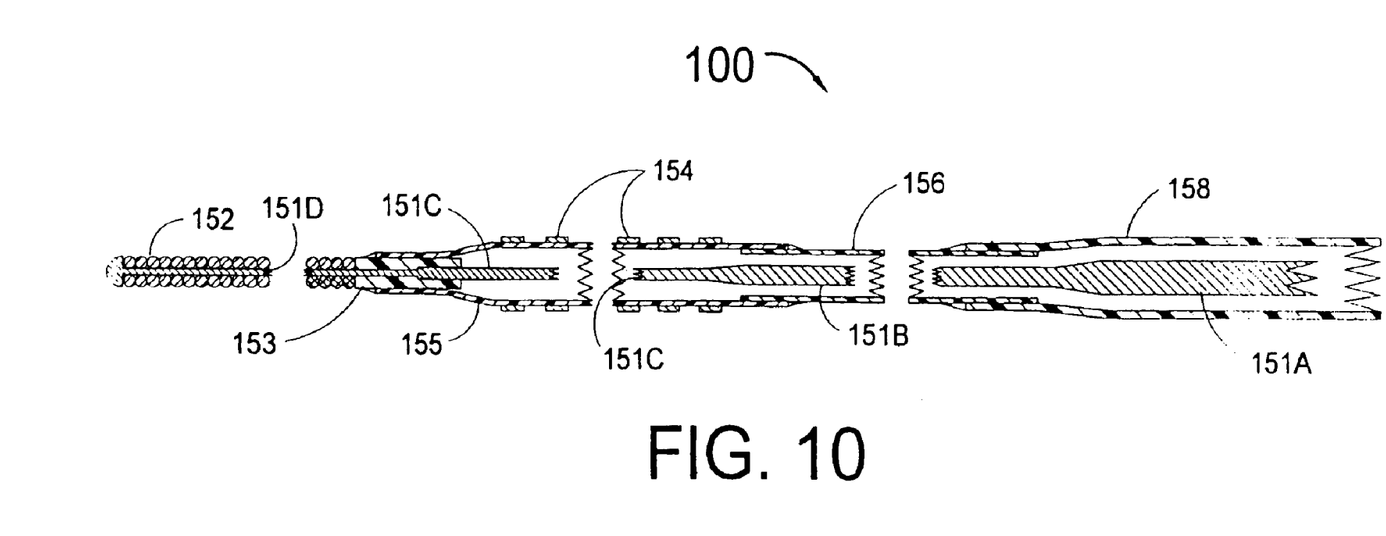
FIG. 10 is a longitudinal cross section of the distal portion of another embodiment of the present invention that has an elongated core wire extending to the proximal end of the stent delivery system where the section of the core wire within the balloon expandable stent is significantly less stiff than more proximal portions of the core wire.

FIG. 10 illustrates still another embodiment of the present invention. Specifically, FIG. 10 is a longitudinal cross section of a stent delivery system 100 that has an improved metal core wire. Though they are not shown in FIG. 10, it is clearly envisioned that elastic bands such as the elastic bands 16 and 18 of FIGS. 1 and 2 could also be used with but are not required for the stent delivery system 100 of FIG. 10. The stent delivery system 100 has a fixed guidewire 152 with a centrally located distal core wire portion 151D to which a cylindrical shaped plastic piece 153 is attached. The inflatable balloon 155 is joined at its distal end to the plastic piece 153 and joins at its proximal end to a central tube 156. (Folds in the inflatable balloon are not shown in this figure.) A pre-deployment stent 154 is co-axially mounted onto the balloon 155. Ideally, the stent 154 would be coated with a drug coating such as the drug sirolimus. The central tube 156 connects at its proximal end to the distal end of the proximal tube 158. The proximal end of the proximal tube 158 may be similar in structure to the proximal end of the stent delivery system 50 shown in FIG. 7.

The core wire of the stent delivery system 100 is formed in four parts, namely a distal core wire portion 151D, a central core wire portion 51C lying within the balloon 155, a mid-section 151B that extends from the proximal end of the balloon 155 to the proximal end of the tube 156, and a proximal section 151A that extends from the distal end of the tube 158 to the proximal end of the tube 158. The distal core wire portion 151D is centrally located within the fixed guidewire 152 and is located at the distal end of the stent delivery system 100. The distal and central portions of the core wire 151D and 151C are similar in diameter and both are thinner than the sections 151A and 151B. As with the other embodiments, the wire 151D could have a cross section that is flat, square or round. Sections 151A and 151B have a greater cross sectional area to improve pushability and torquability of the system 100 through the coronary anatomy.

The mid-section 151B of the core wire has a decreased cross sectional area as compared to the proximal portion 151A to facilitate bending of the section of the system 100 between the balloon 155 and the proximal tube 158. The length of the mid-section 151B and the tube 156 should be between 5 and 15 cm for best application to the coronary vasculature. As the proximal section including the proximal tube 158 and proximal core wire 151A are intended to lie proximal to the coronary vasculature, they may be less flexible than the sections of the catheter 100 that are more distal. The use of Nitinol shape memory core wires described for the embodiment 50 of FIGS. 5 and 6 is also applicable to the system 100 of FIG. 10.

Various other modifications, adaptations, and alternative designs are of course possible in light of the above teachings. Therefore, it should be understood at this time that within the scope of the appended claims, the invention might be practiced otherwise than as specifically described herein.

What is claimed is:

1. A stent delivery system comprising:
    a balloon catheter having a distal section with an inflatable balloon located at the distal section;
    a stent co-axially mounted on the inflatable balloon; and
    a flexible guidewire attached to and extending distally from the distal section of the balloon catheter, the guidewire having a central core wire therethrough that extends from the guidewire in a proximal direction through the stent delivery system, the central core wire being formed from a shape memory alloy and having a distal portion that has a transition temperature higher than body temperature.

2. The stent delivery system of claim 1 wherein the core wire has a proximal portion proximal to the distal position, and the core wire proximal to the position having a transition temperature below body temperature.

3. The stent delivery system of claim 1 wherein the guidewire is substantially straight over its entire length.

4. The stent delivery system of claim 1 wherein the guidewire has a distal section that is substantially curved.

5. The stent delivery system of claim 1 wherein the guidewire has an outside diameter that is less than 0.035 inches.

6. The stent delivery system of claim 1 wherein the length of the guidewire extending beyond the distal section of the balloon catheter is less than 5 cm.

7. The stent delivery system of claim 1 wherein the balloon has a longitudinal axis and the balloon is wrapped in a spiral around the balloon's longitudinal axis prior to placement of the stent onto the balloon.

8. The stent delivery system of claim 1 wherein the balloon has a proximal section that has the shape of a frustum of the cone when the balloon is fully inflated, and the balloon catheter includes a proximal elastic band that is placed around the proximal section of the balloon prior to balloon inflation.

9. The stent delivery system of claim 1 wherein the balloon has a distal section that has the shape of a frustum of a cone when the balloon is fully inflated and the balloon catheter includes a distal elastic band that is placed around the distal section of the balloon prior to balloon inflation.

10. The stent delivery system of claim 1 wherein the balloon has a proximal end fixedly attached to a central tube having a central lumen with fluid communication to the environment.

11. The stent delivery system of claim 1 wherein the balloon overhang length beyond each edge of the stent is less than 0.5 mm.

12. The stent delivery system of claim 1 wherein the longitudinal length of the stent when deployed is approximately equal to the length of the cylindrical section of the inflated balloon thereby resulting in an approximately zero length of balloon.

13. The stent delivery system of claim 1 wherein the core wire has a first and smaller cross sectional area where it passes through the fixed guidewire and the balloon, and the core wire has a second and larger cross-sectional area for most of the remainder of its where it passes through a proximal tube that extends for most of the length of the stent delivery system.

14. The stern delivery system of claim 1 wherein the core wire has a first and smallest cross-sectional area where it passes through the fixed guidewire and the balloon; a second and largest cross-sectional area for most of the remainder of its length, and has a third cross-sectional area between the first and second cross-sectional areas.

15. The stent delivery system of claim 1 wherein the stent is coated with a medication useful to reduce restenosis.

16. The stent delivery system of claim 1 further including a heater into which the guidewire portion of the stent delivery system can be placed, the heater being capable of raising the temperature of the guidewire to a temperature above the transition temperature for the core wire.

17. The stent delivery system of claim 1 wherein the helical coil surrounding the core wire of the fixed guidewire of the stern delivery system is formed from a high-density metal.

18. A stent delivery system comprising:
    a balloon catheter having a distal section with an inflatable balloon located at the distal section;
    a balloon expandable stent co-axially mounted on the inflatable balloon; and
    a flexible guidewire attached to and extending distally from the distal section of the balloon catheter, the guidewire having a central core wire therethrough that extends through the guidewire and extends from the guidewire in a proximal direction through the stent delivery system, the central core wire being formed with at least three different cross sectional areas, and the central core wire being formed from a shape memory alloy and having a distal portion that has a transition temperature higher than body temperture.

* * * * *